US00PP34525P3

(12) United States Plant Patent
Koot

(10) Patent No.: US PP34,525 P3
(45) Date of Patent: Aug. 30, 2022

(54) ***BUDDLEJA* PLANT NAMED 'BOTEX 003'**

(50) Latin Name: *Buddleja davidii*
Varietal Denomination: Botex 003

(71) Applicant: Botanic Experience B.V., Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 17/557,032

(22) Filed: Dec. 20, 2021

(65) Prior Publication Data

US 2022/0201913 P1 Jun. 23, 2022

(30) Foreign Application Priority Data

Dec. 23, 2020 (QZ) ..... PBR 20203389

(51) Int. Cl.
*A01H 6/00* (2018.01)
*A01H 5/02* (2018.01)

(52) U.S. Cl.
USPC ..... Plt./242
CPC ..... *A01H 6/00* (2018.05); *A01H 5/02* (2013.01)

(58) Field of Classification Search
USPC ..... Plt./242
See application file for complete search history.

*Primary Examiner* — Annette H Para
(74) *Attorney, Agent, or Firm* — Penny J. Aguirre

(57) ABSTRACT

A new cultivar of *Buddleja* plant named, 'Botex 003', that is characterized by its compact and upright plant habit, its flowers that are white in color, its neat and naturally oblong plant shape, its very floriferous blooming habit, and its flowers that have a pleasant fragrance.

2 Drawing Sheets

Botanical classification: *Buddleja davidii.*
Variety denomination: 'Botex 003'.

CROSS-REFERENCE TO A RELATED APPLICATIONS

This application claims priority to European Community Plant Variety Office (CPVO) Plant Breeder's Rights Application No. 2020/3389 filed on Dec. 23, 2020, under 35 U.S.C. 119(f), the entire contents of which is incorporated by reference herein. This application is also co-pending with a U.S. Plant Patent Application filed for a plant derived from the same breeding program from similar parentage that is entitled *Buddleja* Plant Named 'Botex 004' (U.S. Plant patent application Ser. No. 17/557,039).

BACKGROUND OF THE INVENTION

The present invention relates to a new and distinct cultivar of *Buddleja davidii* will be referred to hereafter by its cultivar name, 'Botex 003'. 'Botex 003' is a new shrub grown for use as an ornamental landscape plant.

The new cultivar of *Buddleja* is a selection from an ongoing breeding program conducted by the Inventor in Kaatsheuvel, The Netherlands with the objective of creating new cultivars of *Buddleja* with very neat and compact plant habits combined with unique flower colors and floriferous blooming habits.

The Inventor made a cross in summer of 2018 between an unnamed proprietary plant in the Inventor's breeding program; reference no. 11013 as the female parent and reference no. 19011 as the male parent. The Inventor selected 'Botex 003' in summer of 2019 as a single unique plant amongst the seedlings that resulted from the above cross.

Asexual propagation of the new cultivar was first accomplished by the Inventor using stem cuttings in Kaatsheuvel, The Netherlands in August of 2019. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 003' as a unique cultivar of *Buddleja.*

1. 'Botex 003' exhibits a compact and upright plant habit.
2. 'Botex 003' exhibits flowers that are white in color.
3. 'Botex 003' exhibits a neat and naturally oblong plant shape.
4. 'Botex 003' exhibits a very floriferous blooming habit.
5. 'Botex 003' exhibits flowers that have a pleasant fragrance.

The female parent of 'Botex 003' differs from 'Botex 003' in having very short inflorescences with flowers that are purple in color and in having a more compact plant habit. The male parent of 'Botex 003' differs from 'Botex 003' in having inflorescences that are more narrow in width and more rounded in shape and in having a more spreading plant habit. 'Botex 003' can also be compared to *Buddleja* cultivars 'White Profusion' (not patented) and 'Botex 004'. 'White Profusion' differs from 'Botex 003' in having a taller plant height, a more vigorous growth habit, and inflorescences that are longer. 'Botex 004' differs from 'Botex 003' in having flowers that are Lilac blue in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Podoslonami, Groen Vandaag, Plantago, Greenport, Gabot, Bloemenkrant, Floricade, Plamntipp, Hortipoint, CG Concept, Stad+Groen, Floranews, Tuinzaken, Handel & Techniek, Van Son & Koot BV, KVBC, Perishablenews, Hortweek, Buddlejagarden, Boom-in-Business, Greenity, and Obst & Garden.

BRIEF DESCRIPTION OF THE DRAWINGS

The accompanying color photographs illustrate the overall appearance and distinct characteristics of the new *Buddleja*. The photographs were taken of a one-year-old plant as grown in a greenhouse in a 19-cm container in Kaatsheuvel, The Netherlands.

The photograph in FIG. 1 provides a side view of the overall plant habit of 'Botex 003' in bloom.

Figure 1:
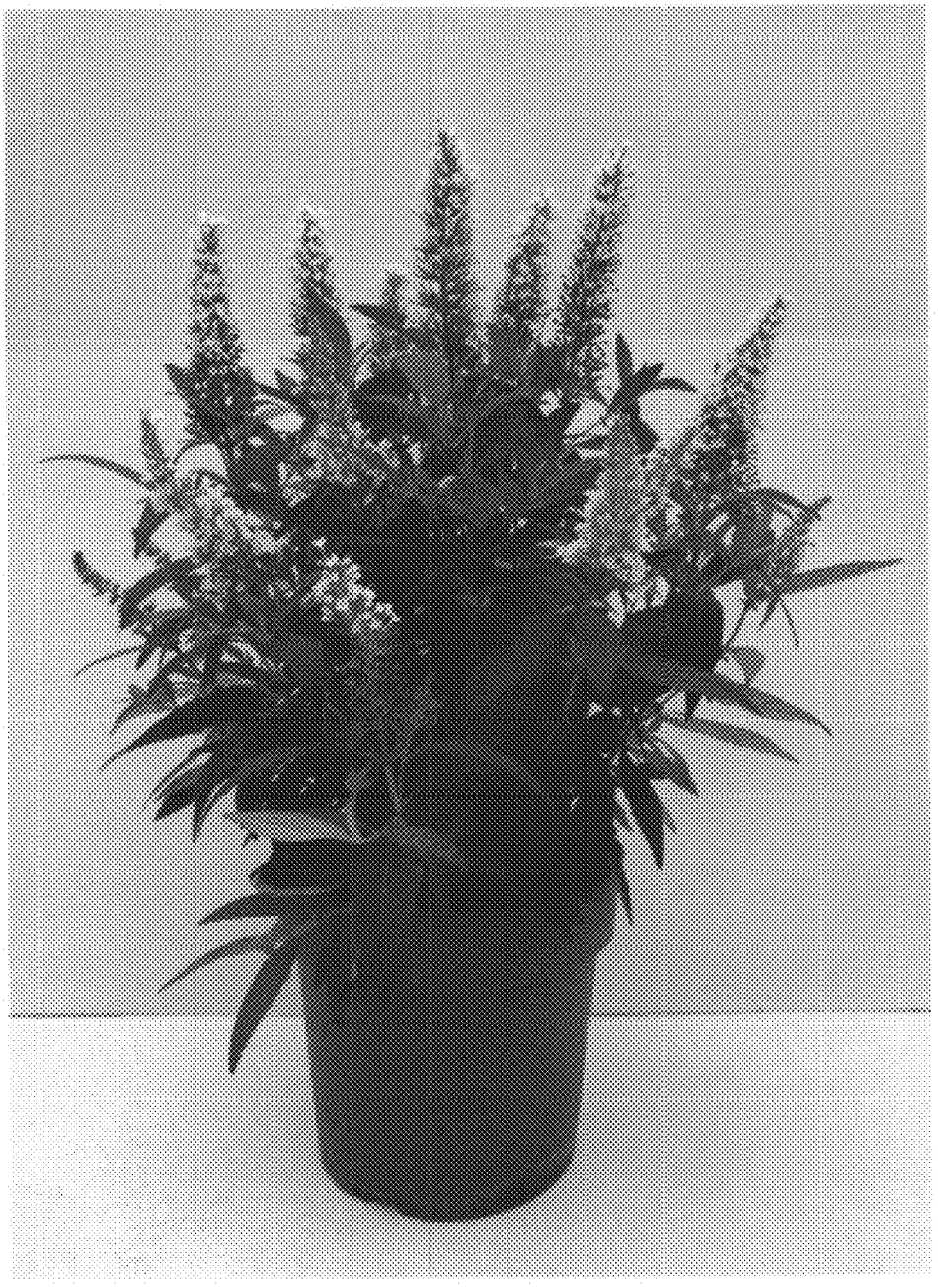
Figure 2:
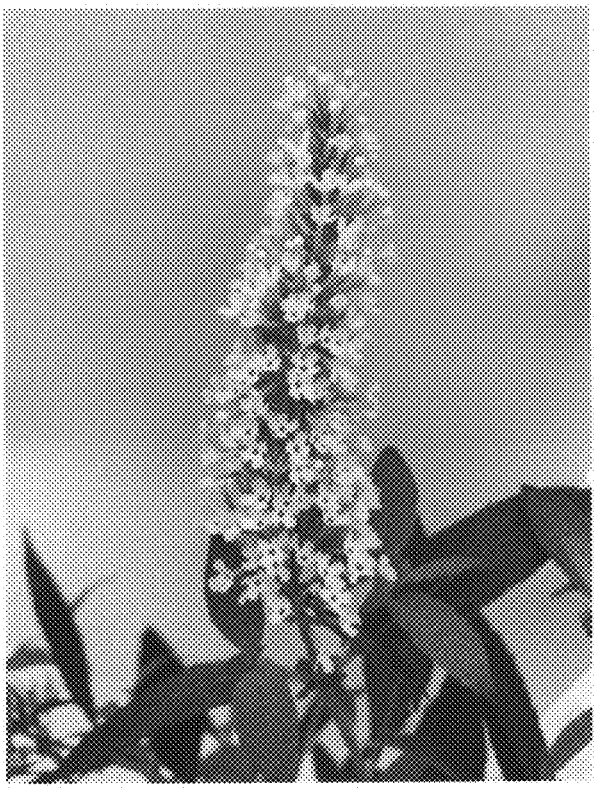

The photograph in FIG. 2 provides a close-up view of an inflorescence of 'Botex 003'.

Figure 3:
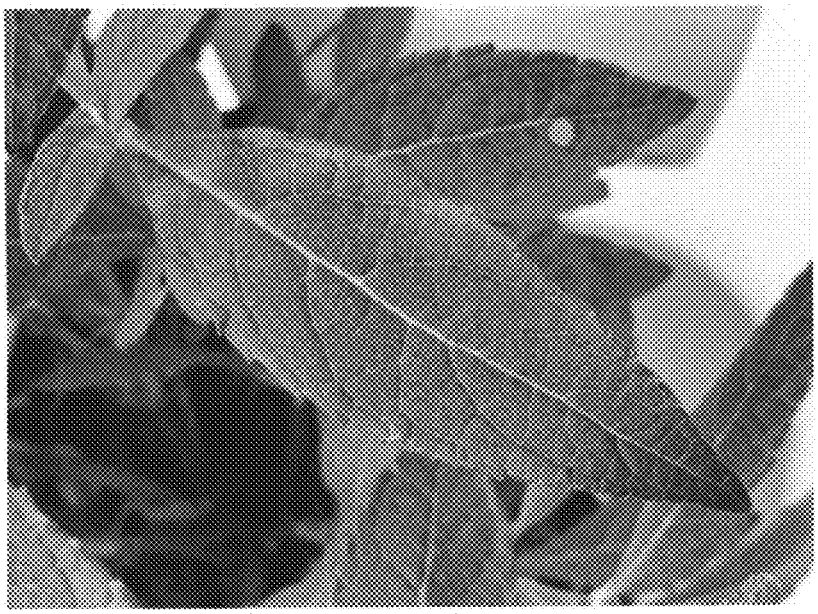

The photograph in FIG. 3 provides a close-up view of the foliage of 'Botex 003'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 19-cm containers in Kaatsheuvel, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—July to October in The Netherlands.

*Plant type.*—Deciduous perennial shrub.

*Plant habit.*—Compact, upright-rounded, dense.

*Plant size.*—An average of 37 cm in height and 39 cm in width as a one-year-old plant in a container and reaches 80 cm in height and 80 to 90 cm in spread as grown in the landscape.

*Cold hardiness.*—At least in U.S.D.A. Zone 5.

*Diseases and pests.*—No susceptibility and resistance to diseases or pests has been observed.

*Propagation.*—Stem cuttings.

*Root description.*—Fibrous.

*Root development.*—An average of 8 weeks to initiate roots and eight weeks to fully root as a young plant in a P9 container.

*Growth rate.*—Vigorous.

Branch description:

*Branch shape.*—Quadrangular.

*Branch color.*—Young stems; 145B, mature stems; 199A.

*Branch strength.*—Strong.

*Branch size.*—An average of 22 cm in length and 3 mm in diameter.

*Branch surface.*—Pubescent.

*Branch internode length.*—Average of 2.7 cm.

*Branching.*—2 main branches, 11 secondary branches.

Foliage description:

*Leaf shape.*—Narrowly elliptical to elliptical.

*Leaf division.*—Simple.

*Leaf base.*—Attenuate.

*Leaf apex.*—Acute.

*Leaf fragrance.*—None.

*Leaf venation.*—Pinnate, color; upper surface 144A, lower surface 191D, main vein 145B.

*Leaf margins.*—Serrate.

*Leaf arrangement.*—Opposite.

*Leaf attachment.*—Petiolate.

*Leaf surface.*—Both sides are smooth, matte, and pubescent.

*Leaf size.*—An average of 8 cm in length and 2.1 cm in width.

*Leaf quantity.*—8 to 10 per stem.

*Leaf color.*—Young upper surface; 137C, base 145C, young lower surface; 191A, mature upper surface; 137A, mature lower surface; 191D.

*Petioles.*—An average of 6 mm in length and 1.5 mm in diameter, medium to high strength, both surfaces 145B in color, both surfaces smooth, glabrous, and slightly pubescent.

Inflorescence description:

*Inflorescence type.*—Compound terminal and axial panicles.

*Inflorescence size.*—An average of 11.5 cm in height, 6.5 cm in width.

*Flower fragrance.*—Sweet, pleasant and light strength.

*Lastingness of flowers.*—An average of 5 days, persistent, inflorescence is semi-indeterminate.

*Flower buds.*—Oblong, average of 1 cm in length and 1.5 mm in diameter, N155C in color.

*Flower aspect.*—Upright.

*Flower quantity.*—An average of 150 flowers per inflorescence.

*Flower type.*—Single, salverform.

*Flower surface.*—All surfaces glabrous and smooth.

*Flower size.*—An average of 1 cm in height, 6 mm in diameter, flower throat; 3 mm in length, 1 mm in diameter, flower tube; 3 mm in length, 1 mm in diameter.

*Peduncles.*—An average of 2.2 cm in length and 2.5 mm in diameter, held erect, 145A in color, strong, glossy and pubescent surface.

*Pedicels.*—An average of 2 mm in length and 1 mm in diameter, held at an average angle of 45°, 145B in color, strong, surface is glossy and pubescent.

*Calyx.*—Campanulate in shape, an average of 2 mm in depth and 1 mm in diameter.

*Sepals.*—4, 1 whorl, rotate arrangement, fused into a campanulate shape, 3.5 mm in length, 1.5 mm in width, lanceolate in shape, acute apex, fused base, entire margin, both surfaces are matte and slightly pubescent, color; when opening and fully open upper and lower surface 145A.

*Petals.*—Average of 4, rotate, fused into salverform, 1 whorl, roughly spathulate in shape, slightly undulate margin, rounded apex, an average of 3.5 mm in length and 2 mm in width, outer and inner surface is glabrous, velvety and matte, color; upper and lower surface when opening and fully open N155B, flower throat 21B, flower tube young 8C, mature 21B.

Reproductive organs:

*Gynoecium.*—1 pistil, 2 mm in length, style; an average of 2 mm in length, 145D in color, stigma; elongated, 1 mm in length and 145B in color, ovary is 145D in color.

*Androcoecium.*—Stamens; 4, filament; 3 mm in length and 23A in color, anther; ovate in shape, 1 mm in length, 11D in color, pollen; low in quantity, 11D in color.

*Fruit and seed.*—No seeds or fruit has been observed.

It is claimed:

1. A new and distinct cultivar of *Buddleja* plant named 'Botex 003' as herein illustrated and described.

* * * * *